United States Patent [19]
Attie et al.

[11] Patent Number: 5,472,858
[45] Date of Patent: Dec. 5, 1995

[54] PRODUCTION OF RECOMBINANT PROTEINS IN INSECT LARVAE

[75] Inventors: Alan D. Attie; Daniel G. Gretch; Stephen L. Sturley, all of Madison, Wis.; Nancy E. Beckage, Riverside, Calif.

[73] Assignee: Wisconsin Alumni Research Foundation, Madison, Wis.

[21] Appl. No.: 709,949

[22] Filed: Jun. 4, 1991

[51] Int. Cl.$^6$ ............................. C12P 21/02; C12N 15/09
[52] U.S. Cl. .................. 435/69.6; 435/320.1; 435/172.3; 359/290
[58] Field of Search ................................. 435/69.1, 69.6, 435/320.1

[56] References Cited

PUBLICATIONS

Law et al, J. Biol. Chem, vol. 264, pp. 16335–16338 (1989).
Au, Y. P. T., et al., "A Rapid Apolipoprotein E Radioimmunoassay Using Solid–Phase Staphylococcus Protein: Use of Pooled Plasma as a Secondary Standard," 138 *B.B.R.C.* 455–462 (1986).
Danyluk, G. M. and J. E. Maruniak, "In vivo and in vitro Host Range of *Autographa californica* Nuclear Polyhedrosis Virus and *Spodoptera frugiperda* Nuclear Polyhedrosis Virus," 50 *J. Invert. Path.* 207–212 (1987).
Fraser, M. J. and G. R. Stairs, "Susceptability of *Trichoplusia ni*, *Heliothis zea* (Noctuidae), and *Manduca sexta* (Sphingidae) to a Nuclear Polyhedrosis Virus from *Galleria mellonella* (Pyralidae)," 40 *J. Invert. Path.* 225–259 (1982).
Kelley, J. L. and A. W. Kruski, "Density Gradient Ultracentrifugation of Serum Lipoproteins in a Swinging Bucket Rotor," 128 *Methods in Enzymology* 170–181 (1986).
Kuroda, K., et al., "Synthesis of Biologically Active Influenza Virus Hemagglutinin in Insect Larvae," 63 *J. Virol.* 1677–1685 (1989).
Luckow, V. A., "Cloning and Expression of Heterologous Genes in Insect Cells with Baculovirus Vectors," in Recombinant DNA Technology and Applications (Prokop, A., Bajpai, R., Ho, C., Eds.) (1991).
Maeda, S., "Expression of Foreign Genes in Insects Using Baculovirus Vectors," 34 *Ann. Rev. Entomol.* 351–372 (1989).
Maeda, S., "Increased Insecticidal Effect by a Recombinant Baculovirus Carrying a Synthetic Diuretic Hormone Gene," 165 *B.B.R.C.* 1177–1183 (1989).
Maeda, S., et al., "Production of Human Alpha–Interferon in Silkworm Using a Baculovirus Vector," 315 *Nature* 592–594 (1985).
Marumoto, Y., et al., "Hyperproduction of Polyhedrin–IGF II Fusion Protein in Silkworm Larvae Infected with Recombinant *Bombyx Mori* Nuclear Polyhedrosis Virus," 68 *J. Gen. Virol.* 2599–2606 (1987).
Matsuura, Y., "Baculovirus Expression Vectors: The Requirements for High–Level Expression of Proteins, Including Glycoproteins," 68 J. Gen. Virol. 1233–1250 (1987).
MaxBac™ Baculovirus Expression Kit, Technical Profile Sheet, Invitrogen Corporation (1990) and advertisement for MaxBac™.
McClintock, et al., "Semipermissive Replication of a Nuclear Polyhedrosis Virus of *Autographa californica* in a Gypsy Moth Cell Line," 57 *J. Virol.* 197–204 (1986).
McIntosh, A., et al., "In vitro Host Range of Five Baculoviruses in Leipdopteran Cell Lines," 23 *Intervirology* 150–156 (1985).
Medin, J. A., et al., "Efficient, Low–Cost Protein Factories: Expression of Human Adenosine Deaminase in Baculovirus–Infected Insect Larvae," 87 P.N.A.S. 2760–2764 (1990).
Miyajima, A., et al., "Use of the Silkworm, *Bombyx Mori*, and an Insect Baculovirus Vector for High–Level Expression and Secretion of Biologically Active Mouse Interleukin–3," 58 *Gene* 273–281 (1987).
Sturley, S., et al., "Heterologous Expression of Apolipoproteins," *Molecular Biology of Athrosclerosis* 17–26 (Attie, A. D., ed.) (1990).
Takehara, K., et al., "Co–Expression of the Hepatitis B Surface and Core Antigens Using Baculovirus Multiple Expression Vectors," 69 *J. Gen. Virol.* 2763–2777 (1988).
Vail, P. V. and S. S. Collier, "Comparative Replication, Mortality and Inclusion Body Production of the *Autographa californica* Nuclear Polyhedrosis Virus in *Heliothis sp.*", 75 *Entomol. Soc. Am.* 376–382 (1982).

*Primary Examiner*—Richard A. Schwartz
*Assistant Examiner*—David Guzo
*Attorney, Agent, or Firm*—Quarles & Brady

[57] ABSTRACT

A human lipid-associated plasma protein has been produced in vivo in larvae of the Sphingid insect tobacco hornworm, *Manduca sexta*. The gene for the protein was introduced by recombinant Baculovirus into the body cavity of the larvae, which is a semi-permissive host for the virus. After the larvae had grown further, the hemolymph of the larvae was recovered. The yield of protein produced was much better than could be achieved for the same gene expressed in insect cell culture and a much higher percentage of the protein produced in vivo was associated in lipid particles as compared to the cell culture system. The desired biological activity of the lipid-associated protein was achieved by the in vivo produced protein but not by the protein produced by insect cells in culture.

8 Claims, 1 Drawing Sheet

PRODUCTION OF RECOMBINANT PROTEINS IN INSECT LARVAE

STATEMENT REGARDING FEDERALLY SPONSORED RESEARCH

This invention was made with United States government support awarded by the National Institute of Health (NIH), Grant #HL37251. The United States Government has certain rights in this invention.

FIELD OF THE INVENTION

The present invention relates to the production of recombinant proteins in general, and relates, in particular, to the efficient production of proteins, and particularly lipid-associated proteins, in insect larvae.

BACKGROUND OF THE INVENTION

Through the technique of genetic engineering, it has become possible to transfer genes from one organism to another organism. One of the objectives of this technique has been to enable the production of proteins in organisms which do not natively make the proteins. Thus it has become possible, and quite common, to isolate genes for human proteins, to insert those proteins into bacterial hosts, and then to grow up large quantities of the bacteria which contain the human gene and which express the human gene to make the human protein. From the bacterial host, the human protein can then be recovered through appropriate purification processes.

While this technique has proven efficacious and useful for a wide variety of proteins, it does have some limitations. Bacteria are prokaryotic organisms which thus differ in their expression and processing systems for genetic products from eukaryotic organisms, such as mammals. Many human proteins must be glycosylated in order to have proper biological activity. Glycosylation refers to the process by which sugars are added onto polypeptide chains to make glycoproteins. Bacteria are incapable of glycosylating proteins at all, and therefore are not optimal hosts for the production of such glycoproteins. Therefore interest has centered in other eukaryotic protein expression systems, notably yeast and insect cells in culture, as possible hosts for the production of recombinant proteins which might be more appropriately glycosylated.

For this reason, and related reasons, there has been effort directed toward the tissue culturing of insect cells in order to serve as recombinant hosts for the production of human proteins. Several systems have been developed for the culture of insect cells in vitro, and vectors have been developed which are capable of transferring foreign DNA into susceptible insect cells. The transforming vectors are most commonly made from a group of insect pathogenic virus known as Baculoviridae, the viruses being known as Baculoviruses. Baculoviruses are characterized by a circular double-stranded DNA genome and a rod-shaped enveloped virion. Through the use of such Baculovirus vectors, genes can be inserted into insect cells in culture, and human proteins can be made by those insect cells. While the glycosylation pattern of proteins made in insect cells is not identical to that occurring in mammals, limited glycosylation does occur and it may be sufficient, in some instances, to achieve the required degree of biological efficacy.

Another requirement of some proteins for efficacy is lipid-associations. Some mammalian proteins, notably including plasma proteins, require association with lipid particles to form lipoprotein particles in order to have appropriate biological activity. Such proteins have not been efficiently produced in non-mammalian hosts to date.

As stated above, most of the activity in production of proteins in insect cells has been directed toward propagation of insect cells in culture. Such efforts have focused on the fall armyworm, *Spodoptera frugiperda*. The cell lines have been developed also from other insects such as the cabbage looper, *Trichoplusia ni* and the silkworm, *Bombyx mori*. It has also been suggested that analogous cell lines can be created using the tobacco hornworm, or *Manduca sexta*. It has been proposed that the large scale propagation of cultured insect cells can be used for making recombinant proteins of biological interest, by the culturing of such cells in large scale bioreactors, and then the recovery of the recombinant proteins therefrom.

Another approach to the production of recombinant proteins is based on the use of live insect larvae. Such an approach uses, in effect, the insect larvae as a factory for the manufacture of the desired gene product. The gene must be introduced into the larvae, and allowed to proliferate, and then the hemolymph recovered from the larvae so that the proteins can be isolated therefrom. Baculovirus have been used to introduce genes into silkworm larvae, *Bombyx mori*. Silkworm was selected because they have been propagated for many years for the production of silk, and therefore the protocols for their cultivation and management are well worked out. Silkworms also have rapid growth, and reasonable disease resistance, so they can be reared in large numbers under sterile conditions. In Japan, in particular, automated feeding machines and artificial diets for silkworms have been developed thereby further facilitating the growth of those insects.

SUMMARY OF THE PRESENT INVENTION

The present invention is summarized in that a method for the production of recombinant proteins in insect larvae includes the steps of creating copies of a gene coding for the production of a lipid-associated recombinant protein and including flanking regulatory sequences effective to express the protein in insect cells, transferring copies of the genes into a Baculovirus capable of mediating expression of the inserted genes into insect cells, inserting the recombinant Baculovirus into the body cavity of larvae of *Manduca sexta*, fostering the growth of the *Manduca sexta*, and bleeding the hemolymph of the Manduca sexta larvae so that the lipid-associated recombinant proteins may be recovered therefrom.

It is an advantage of the present invention in that a system is described for the production of lipid-associated proteins which permits the production of proper association between the recombinant proteins and lipid molecules resulting in yields of biologically active protein which cannot be achieved using insect cell cultures.

It is an object of the present invention to provide a system for the production of recombinant proteins in insect larvae which is more convenient and results in higher efficiency and greater production of recombinant proteins than prior art systems.

It is a further object of the present invention to enable the production of human apolipoproteins in insect hosts, so that the apolipoproteins can be readily manufactured for therapeutic applications.

Other objects, advantages and features of the present invention will become apparent from the following specification when taken in conjunction with the accompanying drawings.

DESCRIPTION OF THE INVENTION

Figure 1:
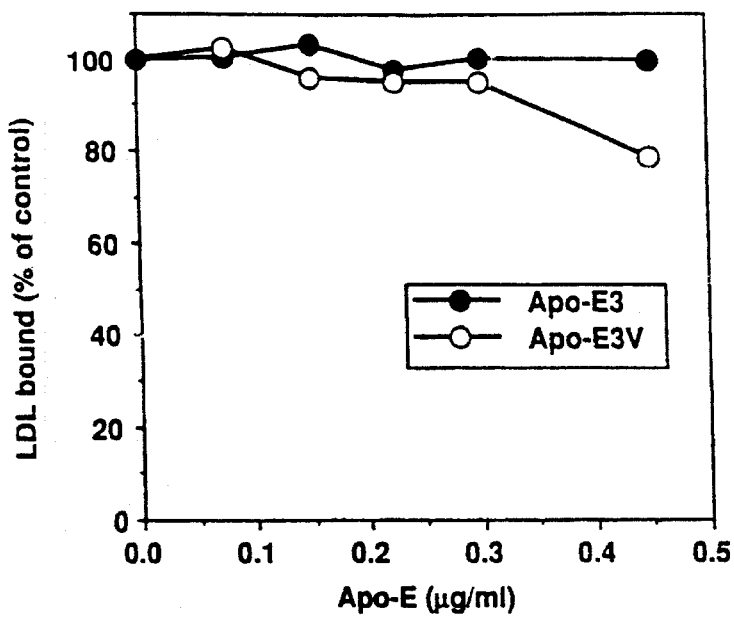
FIG. 1 is a graphical representation of the results obtained in an LDL binding assay of recombinant Apolipoprotein-E (Apo-E) produced in in vitro insect cell culture.

In accordance with the present invention, heterologous proteins are produced in the hemolymph of larvae of Sphingid insects, such as *Manduca sexta*. It has been found that surprisingly high levels of human proteins can be produced in larvae of *Manduca sexta* and further, and also surprisingly, it has been found that lipid associated proteins produced in *Manduca sexta* larvae are sufficiently complexed with lipids so as to be biologically active, a result not possible using techniques of protein production in insect cells in culture.

Using the present invention, a production system for the manufacture of recombinant human proteins in live whole insects is envisioned. The particular insect which is to be utilized, *Manduca sexta*, has the advantage of being a semi-permissive host for recombinant AcNPV Baculovirus, thereby theoretically enabling the titer of biologically effective proteins to rise to higher levels than can be achieved in insects which are more sensitive to viral infection. It has also been found that a human apolipoprotein, when expressed in live larvae is secreted into the hemolymph in correct lipid-associated form, whereas the protein expressed in insect cells in tissue culture was not secreted in a lipid-associated form. This phenomenon facilitates the recovery of purified human protein, since the protein has already been secreted from the host tissues which manufacture it.

*Manduca sexta*, used in the examples described below, is a member of the Sphingidae family of Lepidopteran insects. The members of the Sphingidae family, referred to as Sphingids, are useful hosts for protein production since they are readily manipulable due to their large larvae. Sphingids are also generally semipermissive hosts to nuclear polyhedrosis virus, and other similar Baculoviruses, used as expression vectors for insect cell gene expression experiments. Host species infected with DNA viruses, like Baculoviruses, are categorized as permissive, semipermissive and nonpermissive. Infected cells of a permissive species experience complete, and relatively rapid, viral DNA and protein synthesis leading to the production of viral progeny and cell lysis. Nonpermissive hosts do not support viral replication and therefore survive viral challenge. Semipermissive hosts support limited viral replication and DNA and protein synthesis, often leading to an incomplete infection cycle. *M. sexta* has been identified as a semipermissive host for the Baculovirus used here, nuclear polyhedrosis virus, Volkman and Goldsmith, *Appl. Environ. Microbiol.*, 44, pp. 227–233 (1982).

The method of the present invention is particularly adapted for use with proteins which in their naturally biologically effective state are associated with lipids. Such lipid associated proteins are common in the circulatory system of higher mammals, and many proteins associated with the regulatory functions in the circulatory system require lipid association in order to be efficacious, such as the apolipoproteins like the one described in the example below. In addition, the success of this strategy in achieving proper lipid association suggests that the same strategy could be utilized for the production of vaccines against viruses with lipoprotein envelopes which may require the proper lipid envelopes in order to elicit the desired immunogenic response in the vaccinated individuals.

While the example described below makes use of a somatic cell transformation of the insect larvae, optimally germ line transformed, or transgenic insects are intended to be within the scope and intent of the present invention. The invention may readily be practiced as described below with Baculovirus vectors on somatic cells in vivo in intact animals. This procedure is both easy and convenient, if research scale or limited quantities of the protein is desired. If industrial production of proteins in *Manduca sexta* is to be launched, it may be preferable to achieve germ line transformation of the insects so that they will constitutively produce the proteins sought to be recovered from the hemolymph animals. If germline transgenic animals are produced, re-infection would not be required for each successive generation. It is particularly advantageous to utilize the hemolymph as the source for the recombinant proteins produced by the animal, since within the hemolymph the proteins can be formed aggregated with the lipids to achieve the biological activity which is sought.

It is an advantage of the use of *Manduca sexta* as the host for the production of recombinant proteins that they are extremely easy and inexpensive to grow, and they propagate particularly well in comparison to insect cell tissue culture cultivation systems. Manduca can grow 4,000 fold in less than one month and will feed on readily available laboratory diets. The larval insects are large, and easy to manipulate, and can be readily raised through successive generations without undue difficulty. The system for fostering the insects is extremely simple and cheap, and produces relatively high titers of recombinant proteins compared to other systems such as mass culture of insect cells.

In order to facilitate the practice of the present invention, several of the routine procedures described in the example below are generally described as follows.

Procedures for Husbandry of *Manduca sexta*

The process of raising *Manduca sexta* begins with eggs. It is preferred that the eggs of *Manduca sexta* are collected daily from the adult chamber (described below) and the eggs thus recovered are placed in an open petri dish inside a square sandwich keeper. After three days, a screen is placed on top of the petri dish and small pieces of food are placed on top of the screen, so that the food is available to the larvae when they hatch. The food pieces are approximately two inch by one inch by one-quarter inch and the larvae may feed through the screen on the food.

The first day that the first instar larvae appear, they are placed in individual one ounce cups on a food piece approximately one-half inch by one-half inch by one inch. This is enough for the individual larvae to consume during its first four instars. The larvae must then be placed in individual cups, since during the later instars, if there is more than one larvae in a cup, they will attack each other. One convenient receptacle which may be utilized for this purpose are one ounce disposable plastic shot glasses, which are available from a variety of restaurant supply companies and which are both economical and disposable.

On the first day of the fifth instar, the larvae are removed from the one ounce cups and placed in five ounce paperboard sundae cups in which an air hole has been made on the lid. The larvae are placed on a fairly large piece of food placed in the bottom of the cups, the food being approximately one inch by one inch by one-half inch. Throughout this time period, the larvae are kept at room temperature in a photoperiod of sixteen hours light eight hours dark. The fifth instar larvae are allowed to remain in the cup and feed until they reach a stage referred to as "EG," which refers to the fact that the larvae go through a stage in which they purge themselves or empty their gut, just prior to pupation. After the larvae have gone through the EG stage, they are removed from the cups and placed in holes in dimensional lumber of redwood (i.e. a 2×4). Holes are drilled in the redwood lumber of approximately one inch in diameter, and the larvae are placed at the bottom of the holes. The holes are then plugged with corks, and the blocks are laid on their sides for approximately ten days to two weeks. This is a sufficient time period for the pupae to develop inside of the holes.

The pupae are dumped out of the redwood blocks, and stored in plastic containers until they turn a very dark color, which takes approximately two weeks. The dark pupae are then placed in a flight chamber to emerge. The adult moths emerge from the pupae, and are confined in a wooden flight chamber approximately two feet by two feet by three feet with a window at the top. The adult moths are kept in the dark, except that at night a lamp with a fifteen watt bulb is placed at the top window to simulate moonlight. A container containing a 40% sucrose solution is also placed in the chamber to serve as a food source for the moths. A stand with Plexiglass leaves attached to it is also placed in the chamber and a real tobacco leaf is placed on top of the plastic ones in the chamber, to serve as a place for the moths to lay their eggs. The adult moths will mate and lay their eggs in the chamber. The flight chamber is vacuumed everyday to remove scales and dead moths and, as stated at the beginning of this procedure, the eggs are collected daily.

*Manduca sexta* Diet (4 liter)

1. Agar-64 g
2. Dry ingredients mixture (this can be weighed out ahead of time and stored in bags in the refrigerator if desired)

- •320 g wheat germ, stabilized
- •144 g casein, vitamin-free
- •128 g sucrose
- • 48 g salt mix, Wesson
- • 64 g yeast, Torula
- • 14 g cholesterol
-     8 g sorbic acid
- •  4 g methylparaban
- •0.4 g streptomycin
- • 20 g ascorbic acid 3. Vitamin mixture 0.900 g nicotinic acid
   •0.450 g riboflavin
   •0.210 g thiamin
    0.210 g pyridoxine -continued 0.210 g folic acid
    0.018 g biotin 900 ml distilled water. Shake and let sit ½ day at room temperature to dissolve. Freeze part of the mixture and store the rest in the refrigerator.

4. 10% formalin 1 part formalin (–37% formaldehyde)

9 parts distilled water

Store at room temperature

5. Wet mixture:

•16 ml linseed oil, raw

•40 ml vitamin mix-shake well before using 94 ml formalin

TO PREPARE DIET:

Heat 3100 ml water with agar mixed in to 90° C. This can be done on a hot plate or by steaming in an autoclave. Allow to cool to 70° C. and pour into blender. With blender on, add wet mix, then dry mix. (The temperature is important because the ascorbic acid will be damaged if the temperature is over 70° C.) Blend the entire mixture for 4 minutes. Pour into pans in the sterile hood and let cool uncovered (hood on) for a couple of hours. Wrap in foil and refrigerate.

Production of Viral Expression Vectors

It is readily known by one of ordinary skill in the art, that heterologous or chimeric foreign gene constructs can be assembled for the expression of foreign or heterologous proteins in insect cells. Typically such foreign genetic constructs include a protein coding region to which are appended appropriate flanking regulatory sequences such as a promoter effective in insect cells to initiate transcription and a transcriptional terminating sequence. Usually the translational start and stop sequences are a part of the cloned or synthesized protein coding region, but they can be artificially assembled and added on to the appropriate ends of the coding sequence, as necessary, if they are not present in the gene clone which is utilized. It has been found that the 5' signal peptide sequence from a human lipoprotein is effective in vivo in insect cells to achieve secretion of the protein into the hemolymph of the insect. Therefore, it would be advantageous for the expression of human proteins that the signal peptide be included in the clone which is transfected into the insect expression vector. Alternatively, a synthetic olegonucleotide sequence can be constructed, analogous to the sequence contained in nucleotides 1 through 61 of SEQ ID NO: 1 below. Such a signal peptide sequence can be added to the 5' end of the gene sought to be inserted into insects to achieve proper secretion patterns.

Once the foreign genetic sequence has been assembled, it is then necessary to package the foreign gene into a Baculovirus vector for insertion into insect cells. This is done using a transfer vector. The example described below utilizes a transfer vector, pAcYM1 provided to the inventors here by Dr. David Bishop and described in *J. Gen. Virology*, 68 pp. 1233–1250 (1987). However, this transfer vector was merely conveniently available, and is not different in effect or ease of use compared to other readily commercially available transfer vectors and Baculovirus expression kits. For example, the Invitrogen Corporation of San Diego, Calif., markets a kit for the expression of foreign genes in insects based on the Baculovirus vector under the trade name MAXBAC. The kit includes Baculovirus stock, and suitable transfer vectors which may be used with the Baculovirus to transfer foreign genes into the Baculovirus for transfection into insect cells. Other similar systems are available from other manufacturers and may be used for the transfer of genes into *Manduca sexta* described in the present application.

It is also described herein that viruses injected into the fourth instar larvae of *Manduca sexta*. Fourth instar larvae were selected for purposes of the example described below based on their high rate of growth and the likelihood that there would be sufficient time period for growth remaining before the virus would replicate to levels which would be adverse to the health of the larvae. While the viral infection system works very well, it may soon be possible to achieve germ line transformed insect hosts, thereby obviating the need for somatic cell infection using the Baculovirus gene expression system.

Recovery of Products

One of the advantages of the system of the present invention is that the foreign proteins expressed are secreted into the hemolymph of the insects. It is therefore relatively easy to recover the suspensions in which the proteins are harbored by recovering the hemolymph from insects which may readily be done by bleeding the insects. Following bleeding, the hemolymph undergoes an oxidation reaction and turns dark and viscous in color. The oxidation reaction can be slowed by keeping the samples refrigerated, and by adding an antioxidant, such as glutathione. The hemocytes can be pelleted from the hemolymph via centrifugation. The resulting supernatant can then be assayed or stored frozen for later use. Suitable protein purification systems including high performance liquid chromatography, affinity binding columns, and other similar techniques known to those of ordinary skill in the art can be utilized to readily further isolate the proteins of interest from the supernatant. It has been found that relatively high titers of protein can be recovered from the hemolymph, with the average of the in vivo insect expression experiments done with the apolipoprotein E being 218 micrograms per milliliter of recovered supernatant. The human protein produced in vivo will display a molecular weight heterogeneity, which may be a reflection of differential glycosylation, just as is observed in mammalian plasma.

Lipid Association

It has been particularly found that the lipid binding characteristics of recombinant proteins produced in vivo in *Manduca sexta* more closely mimic those found in mammals, than the results usually obtained from insect cells in culture. In the blood stream of mammals, and also in the hemolymph of insects, lipid-associated proteins are found in lipoprotein particles. When mammalian Apolipoprotein-E is expressed by insect cells in culture, it has been found that relatively low quantities of the protein expressed have the proper lipid association. It has been found here that when the same protein is produced in vivo in *Manduca sexta* larvae, in excess of one-third of the recovered protein has a lipid-association level associated with that experienced by mammalian lipoproteins in the bloodstream, presumably in excess of 80% lipid.

To assess the biological activity of the lipid association particles, biological testing of the efficacy of those particles for appropriate binding to appropriate cells surface binding proteins may also be studied. It has been found here that for the human protein apolipoprotein-E, that the lipoprotein particles recovered from *Manduca sexta* larvae have the required biological efficacy, and are able to compete effectively for binding to the low-density lipoprotein (LDL) receptor, a natural receptor for this particular protein. In this instance, this is an effective test for biological activity.

Thus it is understood that various mammalian proteins and vaccines can be effectively manufactured in reasonable quantities in vivo in the larvae of *Manduca sexta*. By suitable transfection with the recombinant Baculovirus, the somatic cells of the insect larvae can be infected and induced to create relatively large quantities of heterologous protein in the hemolymph, and in association with the lipids naturally present therein. In this way, lipid associated proteins and lipid protein particles can be created which are biologically active in a fashion which has not readily been achievable before, using insect cell expression systems in in vitro culture. This invention may also be understood with reference to the following examples which are presented by way of illustration and not by way of limitation.

EXAMPLE

Production of Expression Vector

This example describes the expression of the human protein apolipoprotein-E in vivo in the larvae of *Manduca sexta*. The coding sequence for the protein (referred to here as Apo-E3) was obtained in the form of the plasmid pHE53, as described by Wernette et al. *J. Biol. Chem.* 264: pps 9094–9101 (1989). A 1.2 kb fragment derived from the digestion to completion of plasmid pHE53 with the restriction enzymes Eco R1 and Hind III was then tailed with Bam H1 linkers from Promega Corporation. A fragment thus tailed was then cloned into the Bam H1 site of a plasmid designated pAcYM1, which is the vector described in Matsuura et al. *J. Gen. Virol.*, 68 pps. 1233–1250 (1987). The resulting plasmid was designated pAcE3. In addition, another plasmid was obtained for a second version of the cDNA of the human protein in the form of a plasmid pHAE813 as described in McLean et al., *J. Biol. Chem.* 259: pps. 6498–6504 (1984). The cDNA sequence for the Apo-E3 gene in the plasmid pHAE813 had a mutation at amino acid 152, where alanine is substituted by a proline, which is known to be a disruptive point mutation to the biological efficacy of the protein. The defective gene is hereinafter designated Apo-E3V. The Apo-E3V cDNA from the vector pHAE813 was then obtained by digestion of the vector, with the restriction enzymes AatII and Hin f1, and the 1.1 kilobase fragment containing the cDNA was then ligated into the Sma I site of pBLUESCRIPT M13+ (Stratagene). A 6 base pair Bam HI linker from Promega Corporation was then inserted into the Eco RV site of the same plasmid to produce a plasmid designated p52-Bam. This plasmid was then digested with the restriction enzyme Bam H1 and the resulting 1.1 kilobase fragment was ligated into the Bam H1 site of pAcYM1, yielding a vector designated pAcE3V.

Both of the plasmids pAcE3 and pAcE3V were then co-transfected with the wild-type Baculovirus genome of the *Autographa californica* nuclear polyhedrosis virus (AcNPV) into cells of *Spodoptera frugiperda* Sf-21. Recombinant viruses including the genes encoding the Apo-E3 and Apo-E3V genes were selected, plaque purified, and titered by the techniques described in Summers and Smith, A Manual of Methods for Baculovirus Vectors and Insect Cell Culture Procedures, *Texas Agricultural Experimental Sta-*

*tion Bulletin*, (1987), and Miller et al., *Genetic Engineering*, Vol. 8, Plenum Publishers, pps. 277–298 (1986).

Inoculation of Larvae

The larvae of *Manduca sexta* moved through five developmental stages, referred to as instars. The instars were separated by a molting stage in which the insect sheds its skin. Fourth instar larvae at the second day of the fourth instar, when the larvae had an average mass of about 0.5 grams, were injected with $10^6$ plaque forming units (PFU) of recombinant virus. Larvae of this size were selected because their relative ease of handling, and injection at this stage eliminated the possibility of insect pupation before the recombinant protein could be harvested.

Prior to injection, the larvae were sedated by placing them on ice from ten to fifteen minutes. The body mass of the larvae at this stage limited the amount of recombinant volume that could be injected into the open circulatory system during any one injection. $10^6$ PFU of recombinant virus typically took a volume of between 10 and 20 microliters, which was injected into the body cavity using a 50 microliter Hamilton syringe with a 30 gauge needle. The larvae have four sets of prolegs, which are found in their ventral side roughly midway along their body length. The injection was made by inserting the needle into the base of the forward most proleg and delivering the virus into the hemocoel. The first proleg was selected because it is centrally located along the body, thereby optimizing the chances of the virus spread throughout the entire body cavity. The needle was inserted so that it paralleled the ventral surface of the larvae. Following injection of the virus, the needle was retained in place for roughly 10 seconds, to allow the virus to circulate in the body cavity and to minimize the amount of virus that is lost during the small bleeding event that occurs as the needle is removed. Following injection, each larvae was placed on ice for two to three minutes, to limit its activity and to minimize the loss of hemolymph through bleeding. The insect was then returned to its confinement chamber, or cup.

Typically within one to two days after the initial injection, or whenever the insect was large enough, the insect was boosted with $5 \times 10^6$ PFU of the same recombinant virus. The injection was carried out in the same manner as the first injection.

Harvesting Proteins

Six days after infection, the hemolymph of each of the animals was collected. In order to do this, again the insect was sedated on ice. A dissecting scissors was used to make an incision at the first proleg, and general pressure was applied by hand to both ends of the insect. The hemolymph then flowed out of the incision in a drop-wise fashion into a collection vessel. Following the collection, the hemolymph undergoes an oxidation reaction, referred to as melanization, that turns the liquid very viscous and dark in color. The reaction was slowed by keeping the collection samples on ice. The hemolymph was diluted 1:2 with a buffer referred to as PBSI consisting of phosphate buffered saline, pH 7.4, 5 mM glutathione, 0.002% PMSF (phenylene thylsulfonylflouride), and 0.3 mg/ml Benzamidine. The hemolymph samples were then diluted (from 0.5 to 12 ml) with PBSI, and adjusted with NaBr to a density of 1.21 g/ml and centrifuged at 175,000 times gravity for 48 hours in an SW-41 rotor. Following centrifugation, the top 1 ml of the 12 ml in the centrifugation tube was collected and dialized against PBS. These samples, referred to below as the supernatant, were then further analyzed for presence of the desired proteins.

Analysis of Results

The supernatant from the hemolymph samples were subjected to sodium dodecyl sulfate, 10% polyacrylamide gel electrophoresis. The results were consistent with the 35 kilodalton protein expected. To confirm the correctness of the protein sequence, an immunoblotting procedure was performed as described by Burnette, *Anal. Biochem.*, 112, pps. 195–203 (1981). The immunoblotting was performed using anti-human Apo-E monoclonal antibodies, designated 1E and 13E, as described in Takagi et al., *J. Lipid Res.*, 29, pps. 859–867 (1988), and alkaline phosphatase-conjugated goat anti-rabbit, IgG, (Sigma). The immunoblot technique verified the production of the desired protein and the expected size range. Immunoblots on hemolymph from control larvae transfected with the AcNPV virus without a coding region contained therein did not exhibit a band that reacted with the anti-Apo-E antibody.

To assess the distribution of the recovered Apo-E protein across a bouyant density range, 1 ml of culture medium from insect cells in culture (42 hours post-infection) or 0.5 ml hemolymph (6 days post-infection) were underlayered beneath a NaBr step gradient at a density of 1.0178–1.2418 g/ml and subjected to ultracentrifugation in an SW-41 rotor at 175,000 times gravity for 48 hours. Twelve 1 ml fractions were collected from the tops of the centrifugation tubes, and dialized against phosphate buffered saline. Aliquots were assayed for Apo-E by radio-immunoassay.

The results of the above analysis revealed that a protein of a molecular weight of 35 kalodalton, the predicted molecular weight of Apo-E, which was uniquely immunoreactive with 2 monoclonal antibodies raised against human Apo-E was recovered from the hemolymph of the *Manduca sexta* larvae. In parallel experiments conducted with tissues of Sf-21 in culture, the medium contained Apo-E3 concentrations which averaged 4 and 30 micrograms per milliliter at 36 and 60 hours post-infection, respectively, as determined by radioimmunoassay. In the larva 1 hemolymph of *Manduca sexta* which produced the protein in vivo, the average of pooled samples was 218 micrograms per milliliter of Apo-E from Apo-E3, while the protein Apo-E3V was expressed at 128 micrograms per milliliter. The Apo-E produced in vivo displayed molecular weight heterogeneity, possibly due to differential glycosylation, as is observed in mammalian species in human plasma. The assessment of distribution of the range of buoyancy of the Apo-E is a measure of the lipid association properties of the expressed protein. In Apo-E expressed from insect cell tissue culture, less than 1% of the Apo-E was lipid-associated. By contrast, of the Apo-E3 produced in vivo in the *Manduca sexta* larvae, assayed by the same technique, approximately one-third of the protein floated at a density less than 1.02 g/ml, which indicates a density comprised of an excess of 80% lipid. Since insect lipoproteins are not detected at this density in larvae infected with wild-type AcNPV, it would appear that the heterologous Apo-E expressed in the insect cells facilitated the formation of novel lipoprotein particles detected by this assay.

Figure 2:
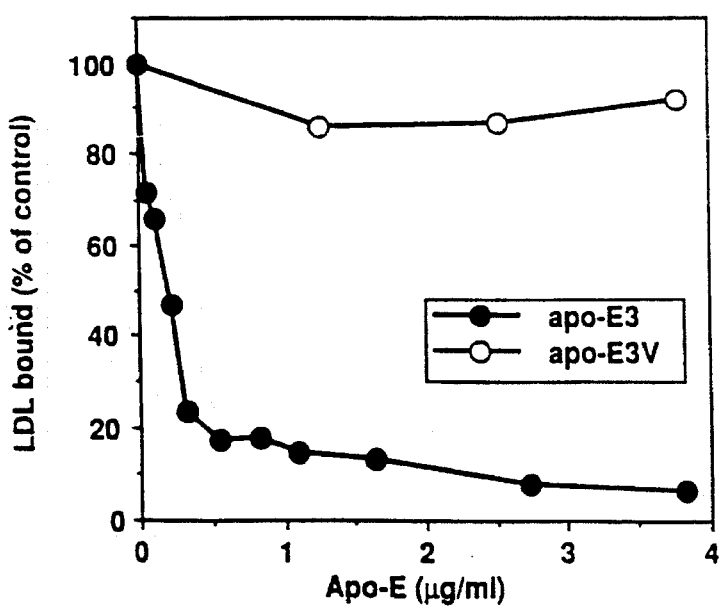
FIG. 2 is a graphical illustration similar to FIG. 1 utilizing recombinant Apo-E produced in in vivo culture of *Manduca sexta* larvae.

To further test the biological activity of the lipoprotein particles containing the recombinant Apo-E, the ability of the particles to compete with LDL for binding to the LDL receptor was tested. CHO cells that stably overexpress the human LDL receptor were used in the receptor binding assay. Several dishes of CHO cells were grown. Each dish was incubated with 0.5 micrograms per milliliter of [$^{125}$I]-LDL in the presence or absence of APO-E particles recovered from the transformed *Manduca sexta* larvae. If the Apo-E is a competent ligand for the LDL receptor, it is able to compete with LDL for receptor binding. In such a case, addition of higher concentrations of Apo-E in successive dishes would result in less [$^{125}$I]-LDL being able to bind to the cells. After incubation, the cells are washed and the [$^{125}$I]-LDL is released from the cell surface with dextran sulfate. The amount of cell associated LDL is determined by measuring the radioactivity in the dextran sulfate released sample. This data is plotted as cell associated LDL versus the amount of Apo-E present. A 100% value corresponds to dishes that had no Apo-E added to them. The results are demonstrated in FIGS. 1 and 2 herewith. FIG. 1 illustrates the results that were achieved for the in vitro production of the proteins from vectors Apo-E3 and Apo-E3V expressed in Sf-21 cells in culture. FIG. 2 illustrates the same experiments conducted for Apo-E produced in the hemolymph of *Manduca sexta* larvae. It can readily be seen that the Apo-E produced in vivo in the intact insect larvae were much more biologically effective in competing for binding to LDL receptor sites. Basically, the Sf-21 cells produced Apo-E that did not effectively compete for LDL receptor binding, apparently because of poor lipid association. The human Apo-E3 produced in the insect larvae was able to compete with LDL for binding to the LDL receptor, and the deficient version of the protein, Apo-E3V, was not able to successfully compete. This indicates that the recombinantly produced molecule produced in the in vivo production system of *Manduca sexta* larvae was biologically efficacious and correct in its lipid association, both results not being achieved through the production of the protein in insect cells in culture.

We claim:

1. A method for the production of apolipoprotein-E comprising the steps of:

(a) preparing a genetic construction including a protein coding sequence for apolipoprotein-E and flanking regulatory sequences effective to express the protein in insect cells;

(b) introducing the genetic construct into a larva of a *Manduca sexta* insect through the use of a recombinant *Autographa californica* nuclear polyhydrosis Baculovirus vector for which the insect is a semi-permissive host;

(c) recovering the hemolymph from the larva;

(d) extracting from the hemolymph one or more fractions containing biologically active apolipoprotein-E in lipid association.

2. A method as claimed in claim 1 wherein the recombinant nuclear polyhydrosis virus is injected into the hemocoel of the larva.

3. A method as claimed in claim 1 wherein the recovering step is performed by bleeding the larva.

4. A method as claimed in claim 1 wherein step (d) is conducted by centrifugal separation of the hemocytes from a supernatant containing the protein.

5. A method as claimed in claim 2 wherein the injection of the nuclear polyhedrosis virus is performed on a fourth instar larvae.

6. A method for the production of a apolipoprotein-E protein in vivo in a lipid associated form comprising the steps of:

(a) preparing a genetic construct including a protein coding sequence for apolipoprotein-E and flanking regulatory sequences effective to express the protein in insect cells and to secrete the protein from the insect cells;

(b) introducing the genetic construct into a *Manduca sexta* larvae through the use of a recombinant AcNPV baculovirus;

(c) culturing the larvae under conditions favorable for the growth of the larvae;

(d) recovering the hemolymph from the larvae; and (e) extracting from the hemolymph a fraction containing the apolipoprotein-E and associated lipid particles.

7. A method as claimed in claim 6 wherein the recombinant nuclear polyhedrosis virus is injected into the hemocoel of the larva.

8. A method as claimed in claim 7 wherein the injection of the polyhedrosis virus is performed on a fourth instar larva.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1157 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Homo sapiens ( i x ) FEATURE:
( A ) NAME/KEY: CDS
( B ) LOCATION: 62..1015

( i x ) FEATURE:
( A ) NAME/KEY: misc_signal
( B ) LOCATION: 62..119

( x ) PUBLICATION INFORMATION:
( A ) AUTHORS: McLean, J W
( C ) JOURNAL: Journal of Biological Chemistry
( D ) VOLUME: 259
( F ) PAGES: 6498-6504
( G ) DATE: 1984
( K ) RELEVANT RESIDUES IN SEQ ID NO:1: FROM 1 TO 1157

( x i ) SEQUENCE DESCRIPTION: SEQ ID NO:1:

```
CCCCAGCGGA GGTGAAGGAC GTCCTTCCCC AGGAGCCGAC TGGCCAATCA CAGGCAGGAA     60

G ATG AAG GTT CTG TGG GCT GCG TTG CTG GTC ACA TTC CTG GCA GGA        106
  Met Lys Val Leu Trp Ala Ala Leu Leu Val Thr Phe Leu Ala Gly
   1               5                  10                  15

TGC CAG GCC AAG GTG GAG CAA GCG GTG GAG ACA GAG CCG GAG CCC GAG      154
Cys Gln Ala Lys Val Glu Gln Ala Val Glu Thr Glu Pro Glu Pro Glu
                20                  25                  30

CTG CGC CAG CAG ACC GAG TGG CAG AGC GGC CAG CGC TGG GAA CTG GCA      202
```

|                                                                                 |      |
|---------------------------------------------------------------------------------|------|
| Leu Arg Gln Gln Thr Glu Trp Gln Ser Gly Gln Arg Trp Glu Leu Ala                 |      |
|         35                  40                  45                              |      |
| CTG GGT CGC TTT TGG GAT TAC CTG CGC TGG GTG CAG ACA CTG TCT GAG                 | 250  |
| Leu Gly Arg Phe Trp Asp Tyr Leu Arg Trp Val Gln Thr Leu Ser Glu                 |      |
|         50                  55                  60                              |      |
| CAG GTG CAG GAG GAG CTG CTC AGC TCC CAA GTC ACC CAA GAA CTG AGG                 | 298  |
| Gln Val Gln Glu Glu Leu Leu Ser Ser Gln Val Thr Gln Glu Leu Arg                 |      |
|     65                  70                  75                                  |      |
| GCG CTG ATG GAC GAG ACC ATG AAG GAG TTG AAG GCC TAC AAA TCG GAA                 | 346  |
| Ala Leu Met Asp Glu Thr Met Lys Glu Leu Lys Ala Tyr Lys Ser Glu                 |      |
| 80                  85                  90                  95                  |      |
| CTG GAG GAA CAA CTG ACC CCG GTA GCG GAG GAG ACG CGG GCA CGG CTG                 | 394  |
| Leu Glu Glu Gln Leu Thr Pro Val Ala Glu Glu Thr Arg Ala Arg Leu                 |      |
|                 100                 105                 110                     |      |
| TCC AAG GAG CTG CAG ACG GCG CAG GCC CGG CTG GGC GCG GAC ATG GAG                 | 442  |
| Ser Lys Glu Leu Gln Thr Ala Gln Ala Arg Leu Gly Ala Asp Met Glu                 |      |
|             115                 120                 125                         |      |
| GAC GTG TGC GGC CGC CTG GTG CAG TAC CGC GGC GAG GTG CAG GCC ATG                 | 490  |
| Asp Val Cys Gly Arg Leu Val Gln Tyr Arg Gly Glu Val Gln Ala Met                 |      |
|         130                 135                 140                             |      |
| CTC GGC CAG AGC ACC GAG GAG CTG CGG GTG CGC CTC GCC TCC CAC CTG                 | 538  |
| Leu Gly Gln Ser Thr Glu Glu Leu Arg Val Arg Leu Ala Ser His Leu                 |      |
|     145                 150                 155                                 |      |
| CGC AAG CTG CGT AAG CGG CTC CTC CGC GAT CCC GAT GAC CTG CAG AAG                 | 586  |
| Arg Lys Leu Arg Lys Arg Leu Leu Arg Asp Pro Asp Asp Leu Gln Lys                 |      |
| 160                 165                 170                 175                 |      |
| CGC CTG GCA GTG TAC CAG GCC GGG GCC CGC GAG GGC GCC GAG CGC GGC                 | 634  |
| Arg Leu Ala Val Tyr Gln Ala Gly Ala Arg Glu Gly Ala Glu Arg Gly                 |      |
|                 180                 185                 190                     |      |
| CTC AGC GCC ATC CGC GAG CGC CTG GGG CCC CTG GTG GAA CAG GGC CGC                 | 682  |
| Leu Ser Ala Ile Arg Glu Arg Leu Gly Pro Leu Val Glu Gln Gly Arg                 |      |
|             195                 200                 205                         |      |
| GTG CGG GCC GCC ACT GTG GGC TCC CTG GCC GGC CAG CCG CTA CAG GAG                 | 730  |
| Val Arg Ala Ala Thr Val Gly Ser Leu Ala Gly Gln Pro Leu Gln Glu                 |      |
|         210                 215                 220                             |      |
| CGG GCC CAG GCC TGG GGC GAG CGG CTG CGC GCG CGG ATG GAG GAG ATG                 | 778  |
| Arg Ala Gln Ala Trp Gly Glu Arg Leu Arg Ala Arg Met Glu Glu Met                 |      |
|     225                 230                 235                                 |      |
| GGC AGT CGG ACC CGC GAC CGC CTG GAC GAG GTG AAG GAG CAG GTG GCG                 | 826  |
| Gly Ser Arg Thr Arg Asp Arg Leu Asp Glu Val Lys Glu Gln Val Ala                 |      |
| 240                 245                 250                 255                 |      |
| GAG GTG CGC GCC AAG CTG GAG GAG CAG GCC CAG CAG ATA CGC CTG CAG                 | 874  |
| Glu Val Arg Ala Lys Leu Glu Glu Gln Ala Gln Gln Ile Arg Leu Gln                 |      |
|                 260                 265                 270                     |      |
| GCC GAG GCC TTC CAG GCC CGC CTC AAG AGC TGG TTC GAG CCC CTG GTG                 | 922  |
| Ala Glu Ala Phe Gln Ala Arg Leu Lys Ser Trp Phe Glu Pro Leu Val                 |      |
|             275                 280                 285                         |      |
| GAA GAC ATG CAG CGC CAG TGG GCC GGG CTG GTG GAG AAG GTG CAG GCT                 | 970  |
| Glu Asp Met Gln Arg Gln Trp Ala Gly Leu Val Glu Lys Val Gln Ala                 |      |
|         290                 295                 300                             |      |
| GCC GTG GGC ACC AGC GCC GCC CCT GTG CCC AGC GAC AAT CAC TGAACGCCGA              | 1022 |
| Ala Val Gly Thr Ser Ala Ala Pro Val Pro Ser Asp Asn His                         |      |
|     305                 310                 315                                 |      |
| AGCCTGCAGC CATGCGACCC CACGCCACCC CGTGCCTCCT GCCTCCGCGC AGCCTGCAGC               | 1082 |
| GGGAGACCCT GTCCCCGCCC CAGCCGTCCT CCTGGGGTGG ACCCTAGTTT AATAAAGATT               | 1142 |
| CACCAAGTTT CACGC                                                                | 1157 |

( 2 ) INFORMATION FOR SEQ ID NO:2:

(i) SEQUENCE CHARACTERISTICS:
  (A) LENGTH: 317 amino acids
  (B) TYPE: amino acid
  (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Lys | Val | Leu | Trp | Ala | Ala | Leu | Leu | Val | Thr | Phe | Leu | Ala | Gly | Cys |
| 1 | | | | 5 | | | | | 10 | | | | | 15 |
| Gln | Ala | Lys | Val | Glu | Gln | Ala | Val | Glu | Thr | Glu | Pro | Glu | Pro | Glu | Leu |
| | | | 20 | | | | | 25 | | | | | 30 | |
| Arg | Gln | Gln | Thr | Glu | Trp | Gln | Ser | Gly | Gln | Arg | Trp | Glu | Leu | Ala | Leu |
| | | | 35 | | | | 40 | | | | | 45 | | |
| Gly | Arg | Phe | Trp | Asp | Tyr | Leu | Arg | Trp | Val | Gln | Thr | Leu | Ser | Glu | Gln |
| | 50 | | | | | 55 | | | | | 60 | | | | |
| Val | Gln | Glu | Glu | Leu | Leu | Ser | Ser | Gln | Val | Thr | Gln | Glu | Leu | Arg | Ala |
| 65 | | | | | 70 | | | | | 75 | | | | | 80 |
| Leu | Met | Asp | Glu | Thr | Met | Lys | Glu | Leu | Lys | Ala | Tyr | Lys | Ser | Glu | Leu |
| | | | | 85 | | | | | 90 | | | | | 95 | |
| Glu | Glu | Gln | Leu | Thr | Pro | Val | Ala | Glu | Glu | Thr | Arg | Ala | Arg | Leu | Ser |
| | | | 100 | | | | | 105 | | | | | 110 | | |
| Lys | Glu | Leu | Gln | Thr | Ala | Gln | Ala | Arg | Leu | Gly | Ala | Asp | Met | Glu | Asp |
| | | 115 | | | | | 120 | | | | | 125 | | | |
| Val | Cys | Gly | Arg | Leu | Val | Gln | Tyr | Arg | Gly | Glu | Val | Gln | Ala | Met | Leu |
| | 130 | | | | | 135 | | | | | 140 | | | | |
| Gly | Gln | Ser | Thr | Glu | Glu | Leu | Arg | Val | Arg | Leu | Ala | Ser | His | Leu | Arg |
| 145 | | | | | 150 | | | | | 155 | | | | | 160 |
| Lys | Leu | Arg | Lys | Arg | Leu | Leu | Arg | Asp | Pro | Asp | Asp | Leu | Gln | Lys | Arg |
| | | | | 165 | | | | | 170 | | | | | 175 | |
| Leu | Ala | Val | Tyr | Gln | Ala | Gly | Ala | Arg | Glu | Gly | Ala | Glu | Arg | Gly | Leu |
| | | | 180 | | | | | 185 | | | | | 190 | | |
| Ser | Ala | Ile | Arg | Glu | Arg | Leu | Gly | Pro | Leu | Val | Glu | Gln | Gly | Arg | Val |
| | | 195 | | | | | 200 | | | | | 205 | | | |
| Arg | Ala | Ala | Thr | Val | Gly | Ser | Leu | Ala | Gly | Gln | Pro | Leu | Gln | Glu | Arg |
| | 210 | | | | | 215 | | | | | 220 | | | | |
| Ala | Gln | Ala | Trp | Gly | Glu | Arg | Leu | Arg | Ala | Arg | Met | Glu | Glu | Met | Gly |
| 225 | | | | | 230 | | | | | 235 | | | | | 240 |
| Ser | Arg | Thr | Arg | Asp | Arg | Leu | Asp | Glu | Val | Lys | Glu | Gln | Val | Ala | Glu |
| | | | | 245 | | | | | 250 | | | | | 255 | |
| Val | Arg | Ala | Lys | Leu | Glu | Glu | Gln | Ala | Gln | Gln | Ile | Arg | Leu | Gln | Ala |
| | | | 260 | | | | | 265 | | | | | 270 | | |
| Glu | Ala | Phe | Gln | Ala | Arg | Leu | Lys | Ser | Trp | Phe | Glu | Pro | Leu | Val | Glu |
| | | 275 | | | | | 280 | | | | | 285 | | | |
| Asp | Met | Gln | Arg | Gln | Trp | Ala | Gly | Leu | Val | Glu | Lys | Val | Gln | Ala | Ala |
| | 290 | | | | | 295 | | | | | 300 | | | | |
| Val | Gly | Thr | Ser | Ala | Ala | Pro | Val | Pro | Ser | Asp | Asn | His | | | |
| 305 | | | | | 310 | | | | | 315 | | | | | |